US005557682A

United States Patent [19]

Warner et al.

[11] Patent Number: 5,557,682

[45] Date of Patent: Sep. 17, 1996

[54] MULTI-FILTER-SET ACTIVE ADAPTIVE CONTROL SYSTEM

[75] Inventors: Jay V. Warner, Stoughton; Kent F. Delfosse; Scott D. Kuhn, both of Madison, all of Wis.

[73] Assignee: Digisonix, Middlelton, Wis.

[21] Appl. No.: 273,919

[22] Filed: Jul. 12, 1994

[51] Int. Cl.[6] .......... A61F 11/06; H03B 29/00

[52] U.S. Cl. .......... 381/71; 381/94

[58] Field of Search .......... 381/72, 71, 94

[56] References Cited

U.S. PATENT DOCUMENTS

| | | | |
|---|---|---|---|
| 4,677,676 | 6/1987 | Eriksson . | |
| 4,677,677 | 6/1987 | Eriksson . | |
| 4,736,431 | 4/1988 | Allie et al. . | |
| 4,815,139 | 3/1989 | Eriksson et al. . | |
| 4,837,834 | 6/1989 | Allie . | |
| 4,987,598 | 1/1991 | Eriksson . | |
| 5,033,082 | 7/1991 | Eriksson et al. . | |
| 5,172,416 | 12/1992 | Allie et al. . | |
| 5,206,911 | 4/1993 | Eriksson et al. . | |
| 5,216,721 | 6/1993 | Melton . | |
| 5,216,722 | 6/1993 | Popovich . | |
| 5,283,834 | 2/1994 | Goodman et al. . | |
| 5,377,276 | 12/1994 | Terai | 381/71 |

FOREIGN PATENT DOCUMENTS

| | | | |
|---|---|---|---|
| 2137600 | 5/1990 | Japan | 381/71 |
| 4190396 | 7/1992 | Japan | 381/71 |
| 5-46185 | 2/1993 | Japan | 381/71 |
| 6-19485 | 1/1994 | Japan | 381/71 |
| 6161466 | 6/1994 | Japan | 381/71 |
| 4226499 | 8/1994 | Japan | 381/71 |

*Primary Examiner*—Curtis Kuntz
*Assistant Examiner*—Minsun Oh
*Attorney, Agent, or Firm*—Andrus, Sceales, Starke & Sawall

[57] ABSTRACT

A multi-filter-set active adaptive control system includes a plurality of output transducer arrays introducing control signals to combine with a system input signal to yield a system output signal. A plurality of error transducers sense the system output signal and provide a plurality of error signals to a plurality of sets of adaptive filters. A plurality of sets of D/A converters are provided at the outputs of the adaptive filters outputting correction signals therethrough. A plurality of sets of A/D converters are provided at the filter inputs and error inputs of the adaptive filters. Various filter sets and combinations are provided.

21 Claims, 6 Drawing Sheets

MULTI-FILTER-SET ACTIVE ADAPTIVE CONTROL SYSTEM

BACKGROUND AND SUMMARY

The invention relates to active adaptive control systems, and more particularly to a multi-filter-set system.

The invention arose during continuing development efforts directed toward active acoustic attenuation systems. Active acoustic attenuation involves injecting a canceling acoustic wave to destructively interfere with and cancel an input acoustic wave. In an active acoustic attenuation system, the input acoustic wave is sensed with an input transducer, such as a microphone or an accelerometer, which supplies an input reference signal to an adaptive filter control model. The output acoustic wave is sensed with an error transducer which supplies an error signal to the model. The model supplies a correction signal to a canceling output transducer, such as a loudspeaker or a shaker, which injects an acoustic wave to destructively interfere with the input acoustic wave and cancel or control same such that the output acoustic wave at the error transducer is zero or some other desired value.

An active adaptive control system minimizes an error signal by introducing a control signal from an output transducer to combine with the system input signal and yield a system output signal. The system input signal is sensed with an input transducer providing a reference signal. The system output signal is sensed with an error transducer providing an error signal. An adaptive filter model has a model input from the reference signal, an error input from the error signal, and outputs a correction signal to the output transducer to introduce the control signal matching the system input signal, to minimize the error signal.

The present invention is applicable to active adaptive control systems, including active acoustic attenuation systems. The present invention provides a system for implementing multichannel active control systems using multiple filters having multiple independent A/D and D/A converters. This system facilitates use of active control for applications requiring large amounts of processor computation time and/or memory by sharing the computational requirements between multiple controllers. The invention significantly reduces parallel processing requirements by using multi-filter-set combinations. The invention may be used to implement multichannel control systems such as shown in U.S. Pat. Nos. 5,216,721 and 5,216,722, incorporated herein by reference.

DETAILED DESCRIPTION

Figure 1:
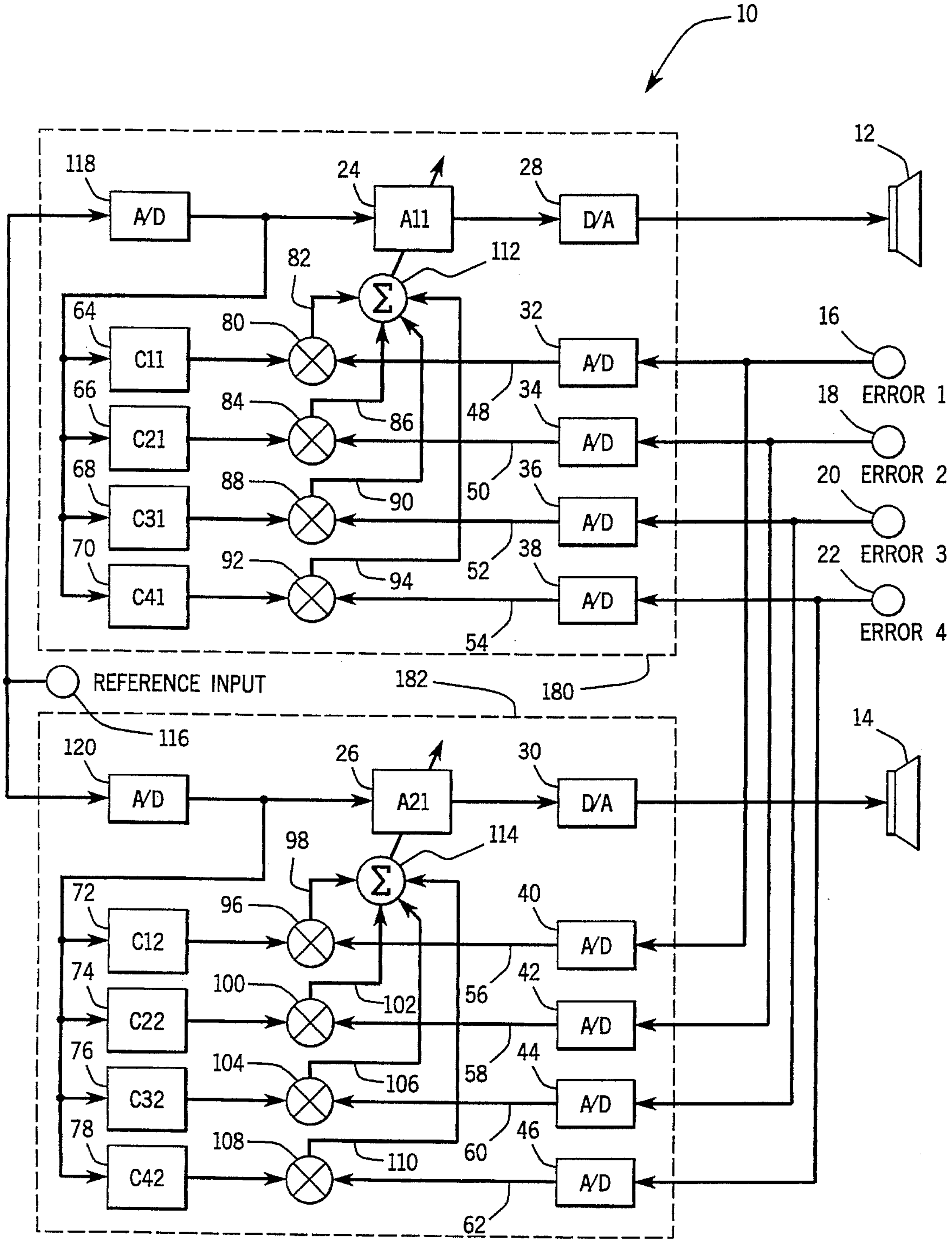
FIG. 1 is a schematic illustration of an active adaptive control system in accordance with the invention.

FIG. 1 shows a multichannel active adaptive control system 10. A plurality of output transducer arrays 12, 14, etc. are provided, each array having at least one output transducer such as a loudspeaker, shaker, or other actuator or controller. The output transducer arrays introduce control signals to combine with a system input signal to yield a system output signal, as in incorporated U.S. Pat. No. 5,216,721 for example at canceling loudspeakers 14 and 210 introducing signals to combine with system input signal 6 to yield system output signal 8, and also for example as shown in U.S. Pat. No. 4,677,676, incorporated herein by reference, showing canceling loudspeaker 14, input signal 6, and output signal 8. A plurality of error transducers 16, 18, 20, 22, etc., such as microphones, accelerometers, or other sensors, sense the system output signal and provide a plurality of error signals. A plurality of A filters 24, 26, etc. are provided, one for each output transducer array 12, 14, etc. Each of the A filters is preferably an LMS, least mean square, FIR, finite impulse response, filter, for example as shown at 12, 302, etc. in the incorporated '721 patent, and as shown at 12 in the incorporated '676 patent, though other types of adaptive filters may be used, including RLMS, recursive least mean square, IIR, infinite impulse response, filters such as shown at 40, 202 in the incorporated '721 patent, and at 40 in the incorporated '676 patent, as well as other adaptive filters. $A_{11}$ filter 24 models the transfer function or acoustic path to output transducer 12. $A_{21}$ filter 26 models the transfer function or acoustic path to output transducer 14. A plurality of D/A, digital to analog, converters 28, 30, etc. are provided, one for each output transducer array 12, 14, etc. Each A filter outputs a correction signal through its respective D/A converter to its respective output transducer array to introduce the control signal. A plurality of sets of A/D, analog to digital, converters are provided, one set for each A filter. Each set has a plurality of A/D converters, one for each error transducer. In FIG. 1, a first set is provided by A/D converters 32, 34, 36, 38, and a second set is provided by A/D converters 40, 42, 44, 46. Each A filter has a plurality of error inputs, one for each A/D converter of its respective set. $A_{11}$ filter 24 has error inputs 48, 50, 52, 54. $A_{21}$ filter 26 has error inputs 56, 58, 60, 62. Each error input receives a respective error signal through its respective A/D converter from its respective error transducer.

A plurality of sets of C filters are provided, one set for each A filter. Each set has a plurality of C filters, one for each error transducer. In FIG. 1, a first set is provided by C filters 64, 66, 68, 70, and a second set is provided by C filters 72, 74, 76, 78. Each set of C filters has an input from the input to the respective A filter. Each C filter of each set has an output combined with the output of a respective A/D converter of the respective set of A/D converters. The output of C filter 64 is multiplied with the output of A/D converter 32 at multiplier 80, and the output resultant product provides weight update signal 82, as in the incorporated '721 and '676 patents. The output of C filter 66 is multiplied by the output of A/D converter 34 at multiplier 84, and the output resultant product provides weight update signal 86. The output of C filter 68 is multiplied by the output of A/D converter 36 at multiplier 88, and the output resultant product provides weight update signal 90. The output of C filter 70 is multiplied by the output of A/D converter 38 at multiplier 92, and the output resultant product provides weight update signal 94. The output of C filter 72 is multiplied by the output of A/D converter 40 at multiplier 96, and the output resultant product provides weight update signal 98. The output of C filter 74 is multiplied by the output of A/D converter 42 at multiplier 100, and the output resultant product provides weight update signal 102. The output of C filter 76 is multiplied by the output of A/D converter 44 at multiplier 104, and the output resultant product provides weight update signal 106. The output of C filter 78 is multiplied by the output of A/D converter 46 at multiplier 108, and the output resultant product provides weight update signal 110. Weight update signals 82, 86, 90 and 94 are summed at summer 112, and the output resultant sum is provided as the weight update signal to A filter 24. Weight update signals 98, 102, 106 and 110 are summed at summer 114, and the output resultant sum is the weight update signal to A filter 26. The C filters model the transfer function or acoustic path from the respective output transducer to the respective error transducer. For example, $C_{11}$ filter 64 models the transfer function to the first error transducer 16 from the first output transducer 12, $C_{21}$ filter 66 models the transfer function to the second error transducer 18 from the first output transducer 12, $C_{31}$ filter 68 models the transfer function to the third error transducer 20 from the first output transducer 12, $C_{41}$ filter 70 models the transfer function to the fourth error transducer 22 from the first output transducer 12, $C_{12}$ filter 72 models the transfer function to the first error transducer 16 from the second output transducer 14, $C_{22}$ filter 74 models the transfer function to the second error transducer 18 from the second output transducer 14, $C_{32}$ filter 76 models the transfer function to the third error transducer 20 from the second output transducer 14, and $C_{42}$ filter 78 models the transfer function to the fourth error transducer 22 from the second output transducer 14. The C filters are preferably provided using a random noise source as shown at 140 in FIG. 19 of the incorporated '676 patent, with a copy of the respective transfer function or acoustic path filter model provided as shown at 144 in FIG. 19 of the incorporated '676 patent, and also as shown at 352, 354, etc. in FIG. 8 of the incorporated '721 patent. It is preferred that each set of C filters have its own random noise source, for example as shown at 140*a*, 140*b* in FIG. 8 of the incorporated '721 patent. Alternatively, the output transducer to error transducer transfer function or acoustic path may be modeled without a random noise source as in U.S. Pat. No. 4,987,598, incorporated herein by reference.

A reference input transducer 116, such as a microphone, accelerometer, or other sensor, senses the system input signal and provides a reference signal as at 42 in the incorporated '721 and '676 patents. A plurality of A/D converters 118, 120, etc., are provided, one for each A filter. Each A filter has a reference input receiving the reference signal through its respective A/D converter from the reference input transducer 116. $A_{11}$ filter 24 models the transfer function or acoustic path to output transducer 12 from input transducer 116. $A_{21}$ filter 26 models the transfer function or acoustic path to output transducer 14 from input transducer 116. The system is applicable to one or more input transducers, one or more output transducers, and one or more error transducers. One or more reference input signals representing the system input signal are provided by one or more reference input transducers such as 116. Only a single reference signal need be provided, and the same such reference signal may be input to each of the adaptive filter models. Such single reference input signal may be provided by a single input microphone, accelerometer or other sensor, or alternatively the reference input signal may be provided by a transducer such as a tachometer which provides the frequency of a periodic system input signal such as from an engine or the like. Alternatively, multiple reference input signals may be used. Further alternatively, the input reference signal may be provided by one or more error signals, in the case of a periodic noise source, for example incorporated U.S. Pat. No. 5,216,722. In FIG. 1, a first filter set combination is shown in dashed line at 180, and a second filter set combination is shown in dashed line at 182.

Figure 2:
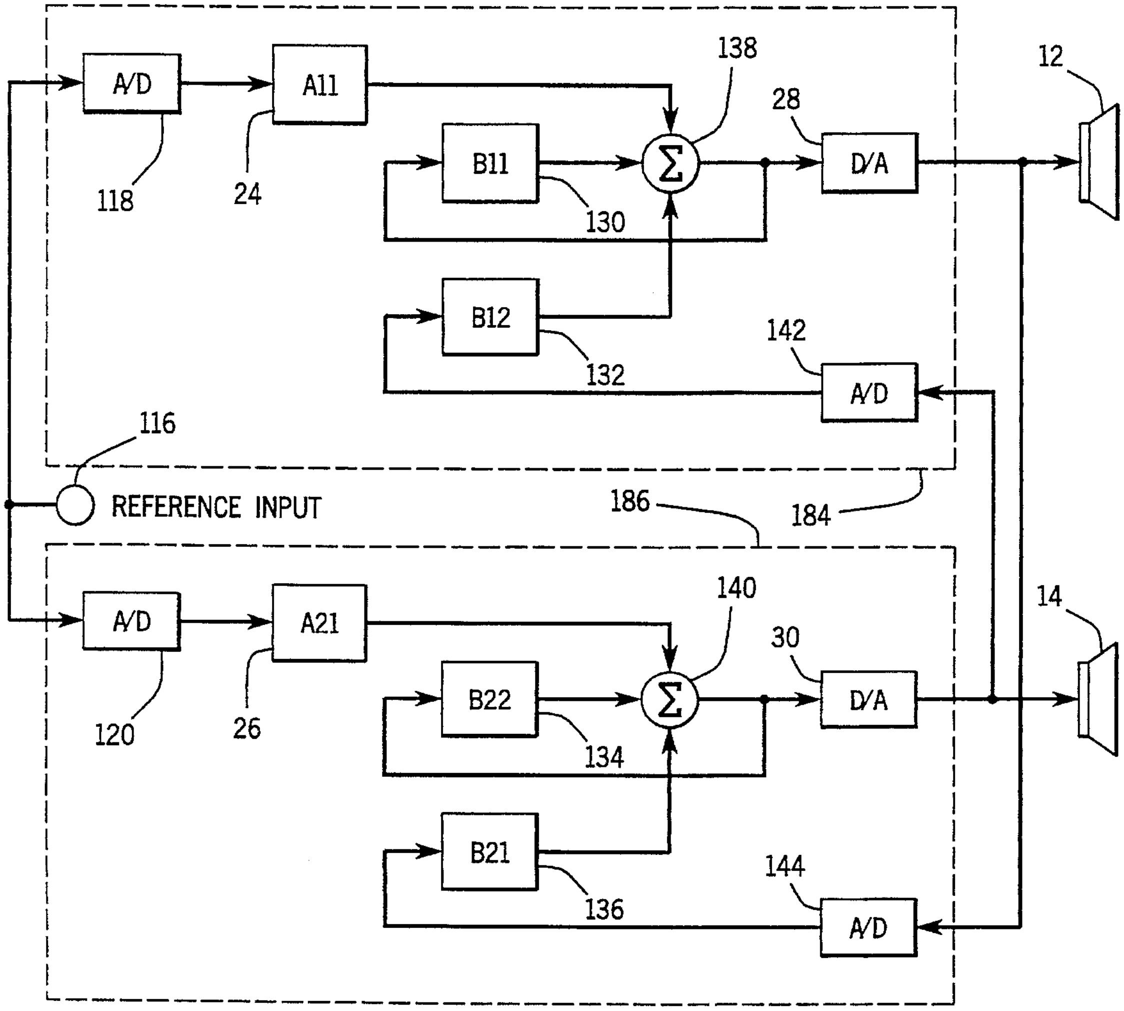
FIG. 2 is similar to FIG. 1 and shows another embodiment.

FIG. 2 uses like reference numerals from FIG. 1 where appropriate to facilitate understanding. A plurality of sets of adaptive B filters are provided, one set for each A filter. Each set has a plurality of B filters, one for each output transducer. Each B filter is preferably an LMS FIR filter provided as in the incorporated '721 and '676 patents, though other filters may be used. A first set is provided by B filters 130 and 132. A second set is provided by B filters 134 and 136. Each A filter has an output summed at a summer with the outputs of the B filters of its respective set, and the output of the summer provides the correction signal. The output of A filter 24 is summed at summer 138 with the outputs of B filters 130 and 132. The output of A filter 26 is summed at summer 140 with the outputs of B filters 134 and 136. A plurality of sets of feedback A/D converters are provided, one set for each A filter. The number of feedback A/D converters in each set is one less than the number of output transducers. In FIG. 2, a first set is provided by A/D converter 142, and a second set is provided by A/D converter 144. Each set has a single member because there are two output transducers. If there were three output transducers, then each set would have two members, etc.

Each set of B filters has a first B filter with an input from the summer of its respective A filter prior to passing through its respective D/A converter. For example, in the first set of B filters, B filter 130 has an input from summer 138 prior to the correction signal passing through D/A converter 28. B filter 134 has an input from summer 140 prior to the $A_{21}$ correction signal passing through D/A converter 30. The remaining B filters of each set have an input from a respective feedback A/D converter receiving a correction signal from the summer of another of the A filters after passing through its respective D/A converter. For example, B filter 132 has an input from A/D converter 142 receiving the correction signal from summer 140 of A filter 26 after passing through D/A converter 30. B filter 136 has an input from feedback A/D converter 144 receiving the correction signal from summer 138 of A filter 24 after passing through D/A converter 28. Each input to each of the remaining B filters first passes through the D/A converter of the other A filter and then passes through the feedback A/D converter of the respective remaining B filter. In FIG. 2, a first filter set is shown at 184, and a second filter set is shown at 186.

Figure 3:
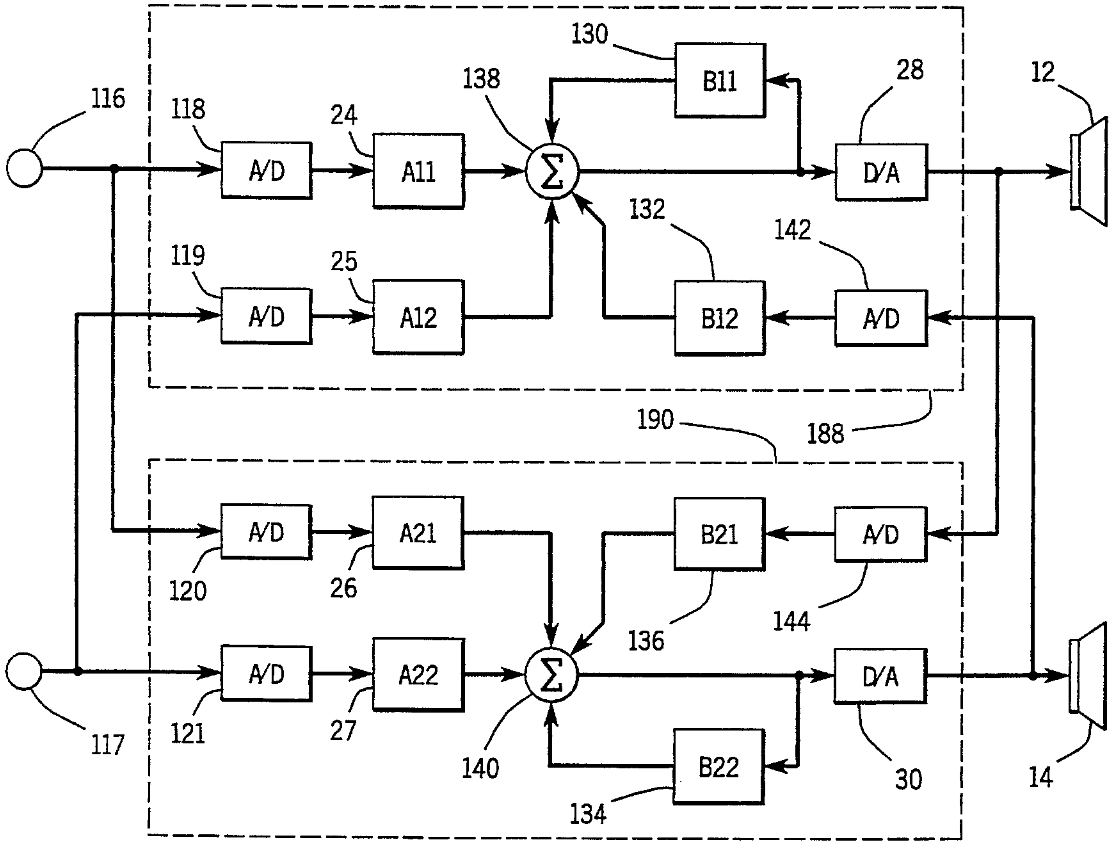
FIG. 3 is similar to FIG. 2 and shows another embodiment.

FIG. 3 uses like reference numerals from above where appropriate to facilitate understanding. A reference input transducer array is provided by one or more reference input transducers 116, 117, etc. $A_{11}$ filter 24 models the transfer function or acoustic path to output transducer 12 from reference input transducer 116. $A_{12}$ filter 25 models the transfer function or acoustic path to output transducer 12 from reference input transducer 117. $A_{21}$ filter 26 models the transfer function or acoustic path to output transducer 14 from reference input transducer 116. $A_{22}$ filter 27 models the transfer function or acoustic path to output transducer 14 from reference input transducer 117. $A_{11}$ filter 24 receives the reference signal from the first reference input transducer 116 through A/D converter 118. $A_{12}$ filter 25 receives the reference signal from the second reference input transducer 117 through A/D converter 119. $A_{21}$ filter 26 receives the first reference signal from reference input transducer 116 through A/D converter 120. $A_{22}$ filter 27 receives the second reference signal from reference input transducer 117 through A/D converter 121. The outputs of A filters 24 and 25 are summed at summer 138 and supplied with the summation of the outputs of B filters 130 and 132 through D/A converter 28 to output transducer array 12. The outputs of A filters 26 and 27 are summed at summer 140 and supplied with the summation of the outputs of B filters 136 and 134 through D/A converter 30 to output transducer array 14. In FIG. 3, a first filter set is shown at 188, and a second filter set is shown at 190.

Figure 4:
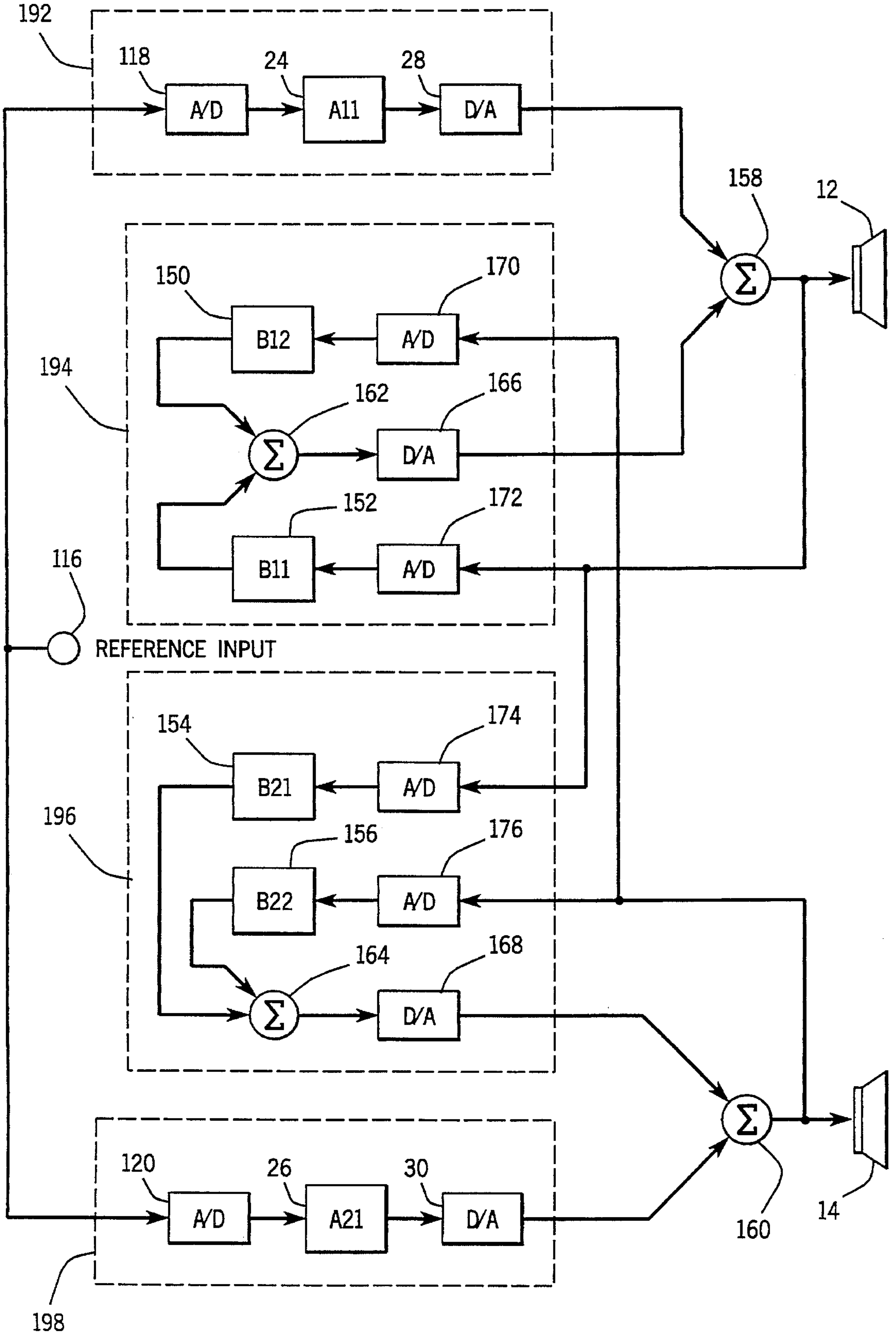
FIG. 4 is similar to FIG. 1 and shows another embodiment.

FIG. 4 uses like reference numerals from above where appropriate to facilitate understanding. A plurality of sets of adaptive B filters are provided, one set for each A filter. Each set has a plurality of B filters, one for each output transducer. A first set is provided by B filters 150 and 152. A second set is provided by B filters 154 and 156. Each B filter is preferably an LMS FIR filter provided as in the incorporated '721 and '676 patents at 22, 314, etc. A first set of summers 158 and 160 is provided, one for each output transducer. A first set of D/A converters is provided by D/A converters 28 and 30, one for each summer. A second set of summers is provided by summers 162 and 164, one for each summer of the first set. A second set of D/A converters is provided by D/A converters 166 and 168, one for each summer of the first set. A plurality of sets of feedback A/D converters is provided, one set for each A filter. Each set has a plurality of A/D converters, one for each B filter of its respective set. The number of feedback A/D converters in each set is equal to the number of output transducers. In FIG. 4, a first set of feedback A/D converters is provided by A/D converters 170 and 172, and a second set of feedback A/D converters is provided by A/D converters 174 and 176. Summer 158 sums the outputs of D/A converters 28 and 166, and supplies the resultant sum to output transducer 12. Summer 160 sums the outputs of D/A converters 30 and 168, and supplies the resultant sum to output transducer 14. Summer 162 sums the outputs of B filters 150 and 152, and supplies the resultant sum through D/A converter 166 to summer 158. Summer 164 sums the outputs of B filters 154 and 156, and supplies the resultant sum through D/A converter 168 to summer 160. B filter 150 has an input through feedback A/D converter 170 from the output of summer 160. B filter 152 has an input through feedback A/D converter 172 from the output of summer 158. B filter 154 has an input through feedback A/D converter 174 from the output of summer 158. B filter 156 has an input through feedback A/D converter 176 from the output of summer 160. In FIG. 4, a first filter set is shown at 192, a second filter set is shown at 194, a third filter set is shown at 196, and a fourth filter set is shown at 198.

Figure 5:
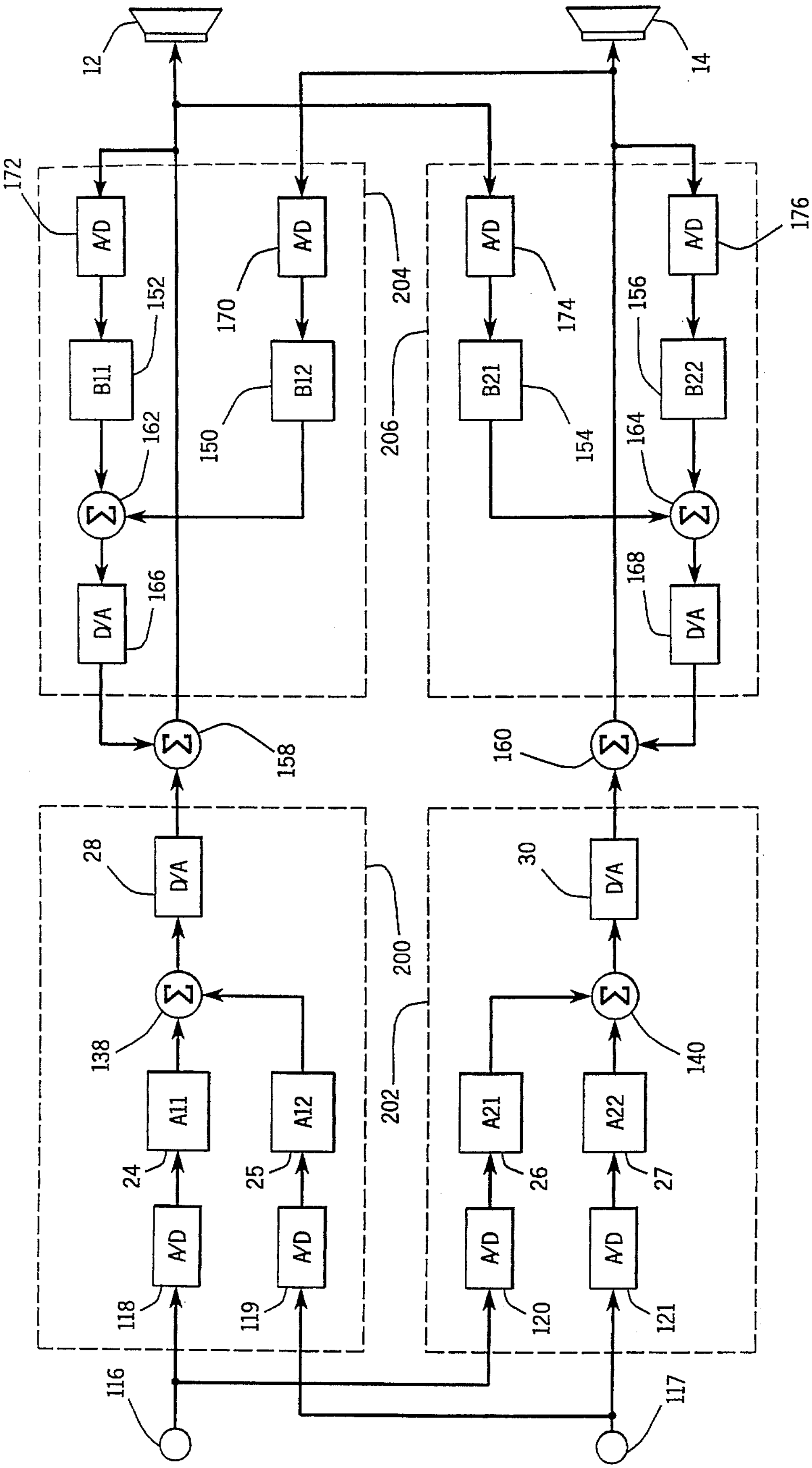
FIG. 5 is similar to FIG. 4 and shows another embodiment.

FIG. 5 uses like reference numerals from above where appropriate to facilitate understanding. Reference input transducer 117 senses the system input signal and provides a second reference signal. A/D converter 118 supplies the first reference signal from reference input transducer 116 to A filter 24. A/D converter 120 supplies the first reference signal to A filter 26. A/D converter 119 supplies the second reference signal from reference input transducer 117 to A filter 25. A/D converter 121 supplies the second reference signal to A filter 27. Summer 138 sums the outputs of A filters 24 and 25 and supplies the resultant sum through D/A converter 28 to summer 158. Summer 140 sums the outputs of A filters 26 and 27 and supplies the resultant sum through D/A converter 30 to summer 160. In FIG. 5, a first filter set is shown at 200, a second filter set is shown at 202, a third filter set is shown at 204, and a fourth filter set is shown at 206.

Figure 6:
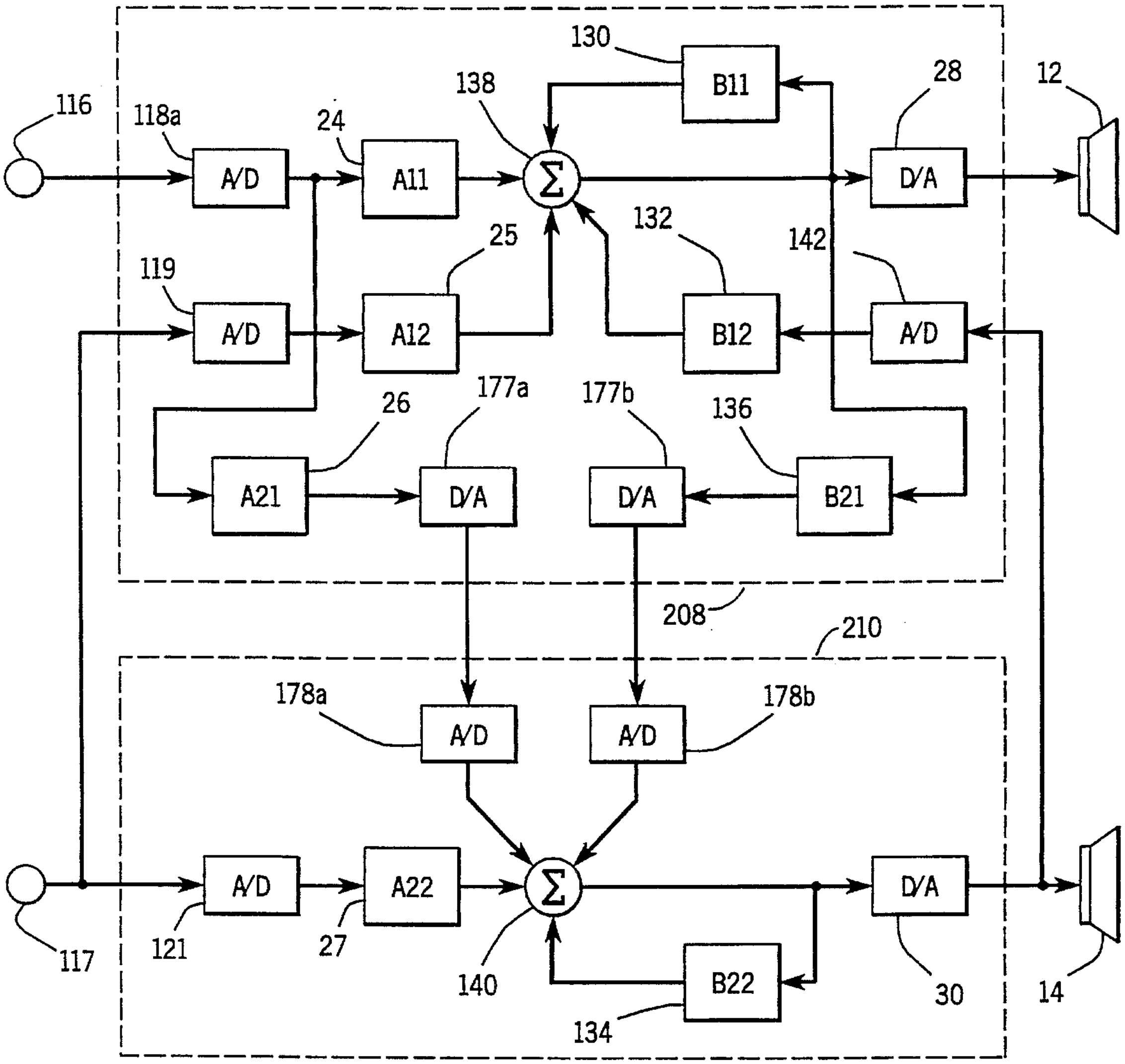
FIG. 6 is similar to FIG. 3 and shows another embodiment.

FIG. 6 uses like reference numerals from above where appropriate to facilitate understanding. A/D converter 118*a* supplies the reference signal from reference input transducer 116 to A filter 24 and to A filter 26. The output of A filter 26 is supplied through D/A converter 177*a* and A/D converter 178*a* to summer 140. The output of B filter 136 is supplied through D/A converter 177*b* and A/D converter 178*b* to summer 140. The input to B filter 136 is supplied from the output of summer 138 prior to passing through D/A converter 28. In FIG. 6, a first filter set is shown at 208, and a second filter set is shown at 210.

It is recognized that various equivalents, alternatives and modifications are possible within the scope of the appended claims. Various filter set combinations have been disclosed. Other filter sets and combinations are possible within the scope of the invention.

We claim:

1. A multi-filter-set active adaptive control system comprising:

a plurality of output transducer arrays introducing control signals to combine with a system input signal to yield a system output signal, each array comprising at least one output transducer;

a plurality of error transducers sensing said system output signal and providing a plurality of error signals;

a plurality of sets of adaptive filters, each set residing on a separate digital signal processor and comprising at least one adaptive filter;

a plurality of sets of D/A converters, one set for each output transducer array, each set comprising at least one D/A converter;

a plurality of sets of A/D converters, each adaptive filter having a plurality of error inputs, each error input receiving a respective error signal through a respective A/D converter from a respective error transducer, wherein at least one error signal from an error transducer is transmitted to at least two A/D converters, each of the two A/D converters being in a separate set of A/D converters.

2. The invention according to claim 1 further comprising a plurality of sets of C filters, one set for each set of adaptive filters each set of C filters comprising a plurality of C filters, at least one C filter for each error transducers, each C filter of each set having an output combined with the output of a respective A/D converter of a respective set of A/D converters.

3. The invention according to claim 1 further comprising:

a reference input transducer array sensing said system input signal, said array comprising at least one reference input transducer providing at least one reference signal;

a plurality of reference A/D converters, one for each of said adaptive filters, each adaptive filter having an input receiving a reference signal through a respective reference A/D converter, wherein the reference signal is transmitted to at least two A/D converters, each of the two A/D converters being in a separate set.

4. The invention according to claim 1 wherein said adaptive filter sets comprise:

a plurality of sets of A filters, each set having an A filter for each reference input transducer, and a plurality of sets of B filters, each set having a B filter for each output transducer array, each A filter having an output summed at a summer with the outputs of the remaining A filters of its respective set and with the outputs of the B filters of its respective set, the output of said summer providing said correction signal; and a plurality of sets of feedback A/D converters, one set for each output transducer array, each set comprising at least one feedback A/D converter.

5. The invention according to claim 4 wherein the number of feedback A/D converters in each set is one less than the number of output transducer arrays, and each set of B filters has a first B filter with an input from the summer of its respective A filter set prior to passing through its respective D/A converter, and wherein each of the remaining B filters of each set has an input from a respective A/D converter receiving a correction signal from the summer of another A filter set after passing through its respective D/A converter, such that each input to each of said remaining B filters first passes through said D/A converter of said other A filter set and then passes through said feedback A/D converter of the respective said remaining B filter.

6. The invention according to claim 1 wherein said adaptive filter sets comprise:

a plurality of sets of A filters, each set having an A filter for each reference input transducer, and a plurality of sets of B filters, each set having a B filter for each output transducer array, and comprising a first set of summers, one for each output transducer array, each summer summing the outputs of the A filters of a respective set, said plurality of sets of D/A converters comprising a first set of D/A converters, one for each summer of said first set of summers, a second set of summers, one for each summer of said first set of summers, a second set of D/A converters, one for each summer of said second set of summers, a third set of summers, one for each D/A converter of said second set of D/A converters, a plurality of sets of feedback A/D converters, one set for each output transducer array.

7. The invention according to claim 6 wherein each set of feedback A/D converters comprises a plurality of feedback A/D converters, one for each B filter of its respective set, the number of feedback A/D converters in each set being equal to the number of output transducer arrays, each summer of said second set of summers summing the outputs of the respective D/A converters of said first set of D/A converters and the outputs of the respective D/A converters of said second set of D/A converters and supplying the resultant sum to the respective output transducer array, each summer of said third set of summers summing the outputs of the respective set of B filters and supplying the resultant sum through the respective D/A converter of said second set of D/A converters to the respective summer of said second set of summers, each B filter having an input through the respective feedback A/D converter of the respective set of feedback A/D converters from the respective summer of said second set of summers.

8. A multi-filter-set active adaptive control system comprising:

a plurality of output transducer arrays introducing control signals to combine with a system input signal to yield a system output signal, each array comprising at least one input transducer;

a plurality of error transducers sensing said system output signal and providing a plurality of error signals;

a plurality of adaptive A filters, one for each of said output transducer arrays, each A filter residing on a separate digital signal processor;

a plurality of D/A converters, one for each output transducer array, each A filter outputting a correction signal through its respective D/A converter to its respective output transducer array to introduce said control signal;

a plurality of sets of A/D converters, one set for each of said A filters, each set comprising a plurality of A/D converters, one for each of said error transducers, each A filter having a plurality of error inputs, one for each A/D converter of its respective set, each error input receiving a respective error signal through its respective A/D converter from its respective error transducer.

9. The invention according to claim 8 comprising a plurality of sets of C filters, one set for each A filter, each set comprising a plurality of C filters, one for each of said error transducers, each set of C filters having an input from the input to the respective A filter, each C filter of each set having an output combined with the output of a respective A/D converter of the respective set of A/D converters, each C filter modeling the transfer function from its respective output transducer to its respective error transducer.

10. The invention according to claim 8 comprising:

a reference input transducer sensing said system input signal and providing a reference signal;

a plurality of reference A/D converters, one for each of said A filters, each A filter having an input receiving said reference signal through its respective reference A/D converter from said reference input transducer.

11. The invention according to claim 8 comprising a plurality of sets of adaptive B filters, one set for each A filter, each set comprising a plurality of B filters, one for each output transducer array, each A filter having an output summed at a summer with the outputs of the B filters of its respective set, the output of said summer providing said correction signal, a plurality of sets of feedback A/D converters, one set for each A filter, the number of feedback A/D converters in each set being one less than the number of output transducer arrays, each set of B filters having a first B filter with an input from the summer of its respective A filter prior to passing through its respective D/A converter, the remaining B filters of each set having an input from a respective feedback A/D converter receiving a correction signal from the summer of another of said A filters after passing through its respective D/A converter, such that each input to each of said remaining B filters first passes through said D/A converter of said other A filter and then passes through said feedback A/D converter of the respective said remaining B filter.

12. The invention according to claim 8 comprising a plurality of sets of adaptive B filters, one set for each A filter, each set comprising a plurality of B filters, one for each output transducer, and comprising a first set of summers, one for each output transducer, said plurality of D/A converters comprising a first set of D/A converters, one for each summer of said first set of summers, and further comprising a second set of summers, one for each summer of said first set of summers, a second set of D/A converters, one for each summer of said first set of summers, a plurality of sets of feedback A/D converters, one set for each A filter, each set comprising a plurality of A/D converters, one for each B filter of its respective set, the number of feedback A/D converters in each set being equal to the number of output transducers, each summer of said first set summing the output of the respective D/A converter of said first set and the output of the respective D/A converter of said second set and supplying the resultant sum to the respective output transducer, each summer of said second set summing the outputs of the respective set of B filters and supplying the resultant sum through the respective D/A converter of said second set of D/A converters to the respective summer of said first set of summers, each B filter having an input through the respective feedback A/D converter of the respective set of feedback A/D converters from the respective summer of said first set of summers.

13. A multi-filter-set active adaptive control system comprising:

first and second output transducer arrays introducing control signals to combine with a system input signal to yield a system output signal, each array comprising at least one output transducer;

a reference input transducer sensing said system input signal and providing a reference signal;

first and second adaptive A filters;

first, second, third and fourth adaptive B filters;

the first adaptive A filter and the first and second adaptive B filters residing on a first digital signal processor;

the second adaptive A filter and the third and fourth adaptive B filters residing on a second digital signal processor;

first and second summers, said first summer summing the output of said first A filter and the outputs of said first and second B filters, said second summer summing the output of said second A filter and the outputs of said third and fourth B filters;

first and second D/A converters, said first D/A converter supplying the output of said first summer to said first output transducer, said second D/A converter supplying the output of said second summer to said second output transducer;

first, second, third and fourth A/D converters, said first A/D converter supplying said reference signal to the input of said first A filter, said second A/D converter supplying said reference signal to the input of said second A filter, said third A/D converter supplying the output of said second D/A converter to the input of said second B filter, said fourth A/D converter supplying the output of said first D/A converter to the input of said fourth B filter, the input to said first B filter being supplied from the output of said first summer, the input to said third B filter being supplied from the output of said second summer.

14. The invention according to claim 13 comprising:

a second reference input transducer sensing said system input signal and providing a second reference signal;

third and fourth adaptive A filters;

fifth and sixth A/D converters, said fifth A/D converter supplying said second reference signal to the input of said third A filter, said sixth A/D converter supplying said second reference signal to the input of said fourth A filter, the outputs of said first and third A filters being summed and supplied with the summation of the outputs of said first and second B filters through said first D/A converter to said first output transducer array, the outputs of said second and fourth A filters being summed and supplied with the summation of the outputs of said third and fourth B filters through said second D/A converter to said second output transducer array.

15. A multi-filter-set active adaptive control system comprising:

first and second output transducer arrays introducing control signals to combine with a system input signal to yield a system output signal, each array comprising at least one output transducer;

a reference input transducer sensing said system input signal and providing a reference signal;

first and second adaptive A filters, the first adaptive A filter residing on a first digital signal processor, and the second adaptive A filter residing on a second digital signal processor;

first, second, third and fourth adaptive B filters, the first and second adaptive B filters residing on a third digital signal processor, and the third and fourth adaptive B filters residing on a fourth digital signal processor;

first, second, third and fourth summers;

first, second, third and fourth D/A converters;

first, second, third, fourth, fifth and sixth A/D converters;

said first summer summing the outputs of said first and third D/A converters and supplying the resultant sum to said first output transducer array;

said second summer summing the outputs of said second and fourth D/A converters and supplying the resultant sum to said second output transducer array;

said third summer summing the outputs of said first and second B filters and supplying the resultant sum through said third D/A converter to said first summer;

said fourth summer summing the outputs of said third and fourth B filters and supplying the resultant sum through said fourth D/A converter to said second summer;

said first A/D converter supplying said reference signal to the input of said first A filter;

the output of said first A filter being supplied through said first D/A converter to said first summer;

said second A/D converter supplying said reference signal to the input of said second A filter;

the output of said second A filter being supplied through said second D/A converter to said second summer;

said third A/D converter supplying the output of said second summer to the input of said first B filter;

said fourth A/D converter supplying the output of said first summer to the input of said second B filter;

said fifth A/D converter supplying the output of said first summer to the input of said third B filter;

said sixth A/D converter supplying the output of said second summer to the input of said fourth B filter.

16. The invention according to claim 15 comprising;

a second reference input transducer sensing said system input signal and providing a second reference signal;

third and fourth adaptive A filters;

seventh and eighth A/D converters, said seventh A/D converter supplying said second reference signal to said third A filter, said eighth A/D converter supplying said second reference signal to said fourth A filter;

fifth and sixth summers, said fifth summer summing the outputs of said first and third A filters and supplying the resultant sum through said first D/A converter to said first summer, said sixth summer summing the outputs of said second and fourth A filters and supplying the resultant sum through said second D/A converter to said second summer.

17. A multi-filter-set active adaptive control system comprising:

an output transducer introducing control signals to combine with a system input to yield a system output signal;

an error transducer sensing the output signal and providing an error signal;

an adaptive digital A filter residing on a first digital signal processor and transmitting a digital output;

a first D/A converter that receives a signal comprised at least in part by the A filter digital output and outputs a first analog signal;

an analog summer that receives the first analog signal and a second analog signal and outputs a correction signal that is transmitted to the output transducer and to an A/D converter;

an adaptive digital B filter that receives digital input from the A/D converter and transmits a digital output, the adaptive B filter residing on a second digital signal processor; and a second D/A converter that receives a signal comprised at least in part by the B filter digital output and outputs the second analog signal.

18. In an active acoustic attenuation system having a system output, the system comprising:

one or more output transducers each outputting a secondary input that combines with the system input to yield the system output;

a plurality of error transducers sensing the system output, each error transducer outputting an analog error signal; and multiple digital filter sets that collectively generate one or more correction signals to drive the one or more output transducers, each digital filter set having at least one adaptive digital filter and at least one A/D converter, the one or more adaptive digital filters of each digital filter set residing on a separate digital signal processor from the one or more adaptive digital filters of the other one or more digital filter sets;

wherein each digital filter set includes at least one A/D converter that receives the same analog error signal as one of the A/D converters in another digital filter set.

19. In an active acoustic attenuation system having a system input and a system output, the system comprising:

one or more output transducers each outputting a secondary input that combines with the system input to yield the system output;

a plurality of input transducers sensing the system input, each input transducer outputting an analog reference signal; and multiple digital filters sets that collectively generate one or more correction signals to drive the one or more output transducers, each digital filter set having at least one adaptive digital filter and a set of A/D converters, the one or more adaptive digital filters of each digital filter set residing on a separate digital signal processor from the one or more adaptive digital filters of the other one or more digital filter sets;

wherein the digital filter set includes at least one A/D converter that receives the same analog reference signal as one of the A/D converters in another digital filter set.

20. In an active acoustic attenuation system having one or more output transducers each outputting a secondary input that combines with a system input to yield a system output, the improvement comprising:

multiple digital filter sets that collectively generate one or more correction signals to drive the one or more output transducers, each digital filter set having:

at least one adaptive digital filter having a digital output, the one or more adaptive digital filters of each digital filter set residing on a separate digital signal processor from the one or more adaptive digital filters of the other one or more digital filter sets;

a D/A converter that receives a digital signal comprised at least in part from the digital output from said adaptive digital filter, the D/A converter transmitting an analog signal from the digital filter set; and an A/D converter that receives an analog signal from at least one of the other multiple digital filter sets.

21. The invention according to claim 20 wherein the analog signal from the digital filter set is one of the correction signals which drives the one or more output transducers.

* * * * *